(12) United States Patent
Cohen

(10) Patent No.: US 8,079,954 B2
(45) Date of Patent: Dec. 20, 2011

(54) VISUAL MEDICAL MONITORING SYSTEM FOR A REMOTE SUBJECT

(75) Inventor: Moshe Cohen, Netanya (IL)

(73) Assignee: Medic4all AG, Zug (CH)

( * ) Notice: Subject to any disclaimer, the term of this patent is extended or adjusted under 35 U.S.C. 154(b) by 0 days.

(21) Appl. No.: 10/496,800

(22) PCT Filed: Dec. 10, 2002

(86) PCT No.: PCT/IL02/00994
§ 371 (c)(1),
(2), (4) Date: Jun. 8, 2004

(87) PCT Pub. No.: WO03/050642
PCT Pub. Date: Jun. 19, 2003

(65) Prior Publication Data
US 2005/0033120 A1    Feb. 10, 2005

Related U.S. Application Data

(60) Provisional application No. 60/337,168, filed on Dec. 10, 2001.

(51) Int. Cl.
*A61B 5/00* (2006.01)
*H04L 12/00* (2006.01)
(52) U.S. Cl. ........ 600/301; 600/300; 128/903; 128/904; 370/260
(58) Field of Classification Search .......... 600/300–301, 600/481, 500, 508, 544–545; 128/903–905, 128/920; 705/2–4; 340/505, 539, 573–574; 348/14.01
See application file for complete search history.

(56) References Cited

U.S. PATENT DOCUMENTS

| 4,710,917 A | * | 12/1987 | Tompkins et al. ............ 709/204 |
| 5,462,051 A | | 10/1995 | Oka et al. |
| 5,544,649 A | * | 8/1996 | David et al. ................... 600/301 |
| 5,772,586 A | * | 6/1998 | Heinonen et al. ............ 600/300 |
| 5,801,755 A | | 9/1998 | Echerer |
| 6,134,504 A | | 10/2000 | Douglas et al. |
| 6,139,494 A | | 10/2000 | Cairnes |
| 6,241,701 B1 | | 6/2001 | Hofmann |
| 6,292,698 B1 | | 9/2001 | Duffin et al. |
| 6,317,039 B1 | * | 11/2001 | Thomason ................. 340/539.1 |
| 6,478,736 B1 | * | 11/2002 | Mault ........................... 600/300 |
| 6,570,974 B1 | * | 5/2003 | Gerszberg et al. ....... 379/218.01 |

(Continued)

FOREIGN PATENT DOCUMENTS

GB    2003276    3/1979

(Continued)

OTHER PUBLICATIONS

Official Action Dated Jun. 3, 2008 From the US Patent and Trademark Office Re.: U.S. Appl. No. 10/496,800.
Official Action Dated Jun. 6, 2006 From the US Patent and Trademark Office Re.: U.S. Appl. No. 10/496,800.
Official Action Dated Feb. 16, 2007 From the US Patent and Trademark Office Re.: U.S. Appl. No. 10/496,800.

*Primary Examiner* — Sam Yao
*Assistant Examiner* — Bobby Soriano

(57) ABSTRACT

The present invention is of a system, which features bi-directional communication for measuring and transferring medical data and for communication with medical personnel. The apparatus is preferably integrated with at least one of, but more preferably both, audio and video conferencing between an external (home and office) subject and a medical service center. The invention is particularly useful for subjects having some type of medical risk who wish to be supervised by a medical service center, as well as supervision for emergency situations.

34 Claims, 3 Drawing Sheets

U.S. PATENT DOCUMENTS

| | | |
|---|---|---|
| 6,579,231 B1 * | 6/2003 | Phipps .......................... 600/300 |
| 6,705,990 B1 * | 3/2004 | Gallant et al. ................. 600/300 |
| 6,723,046 B2 * | 4/2004 | Lichtenstein et al. ........ 600/300 |
| 6,858,006 B2 * | 2/2005 | MacCarter et al. ........... 600/300 |
| 2002/0076034 A1 * | 6/2002 | Prabhu et al. ........... 379/390.02 |
| 2005/0033120 A1 | 2/2005 | Cohen |

FOREIGN PATENT DOCUMENTS

| | | | |
|---|---|---|---|
| WO | WO 01/15056 | * | 1/2001 |
| WO | WO 01/15056 | | 3/2001 |
| WO | WO 01/43631 | | 6/2001 |

* cited by examiner

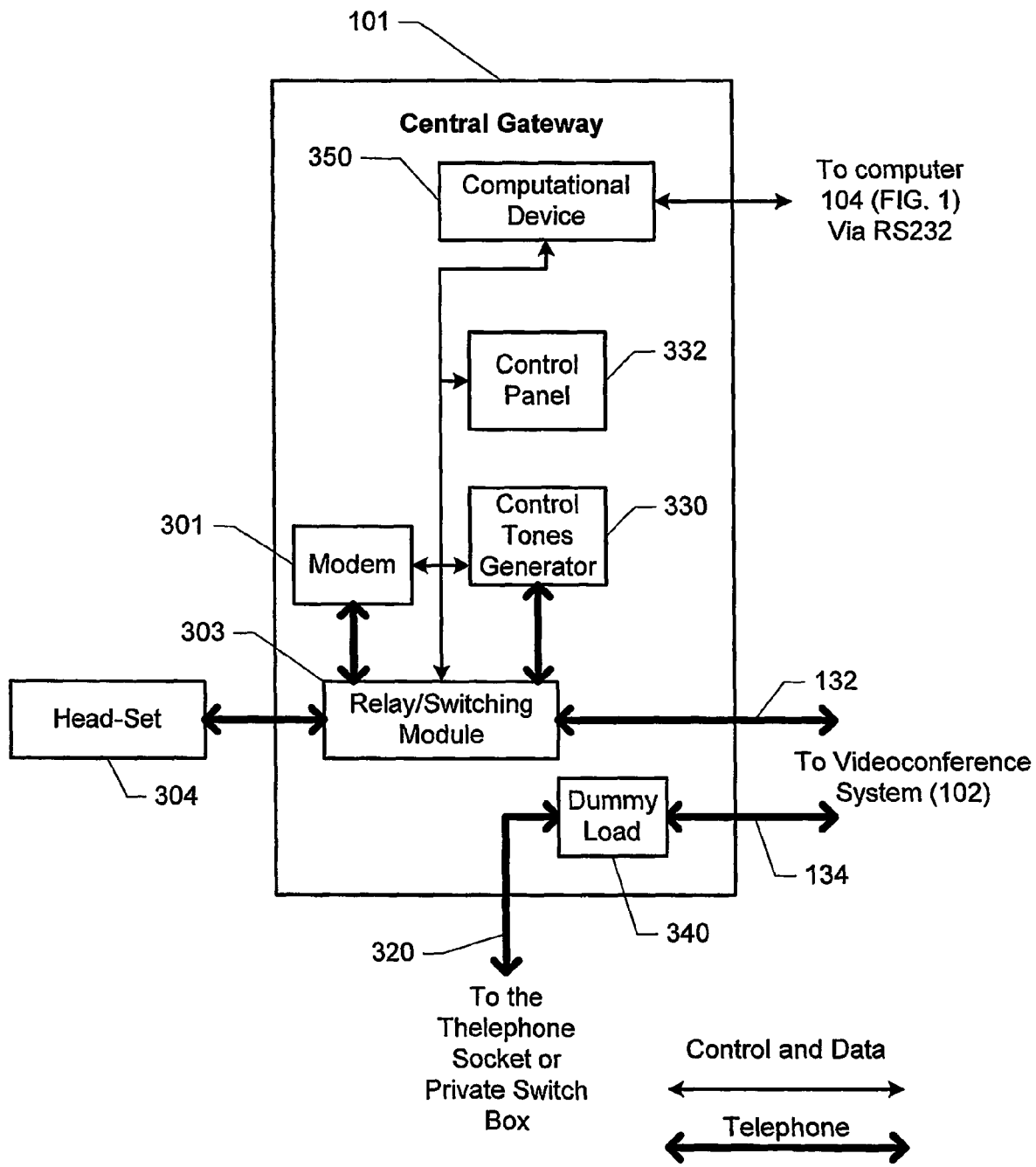

VISUAL MEDICAL MONITORING SYSTEM FOR A REMOTE SUBJECT

CROSS-REFERENCE TO RELATED APPLICATION

This application is a National Phase Application of PCT/IL02/00994 International Filing Date 10 Dec. 2002, which claims priority from U.S. Provisional Patent Application No. 60/337,168 filed on 10 Dec. 2001, entitled, "A VISUAL MEDICAL MONITORING SYSTEM FOR A REMOTE SUBJECT," the subject matter of which is hereby incorporated by reference.

FIELD OF THE INVENTION

The present invention is of a method and apparatus for remote medical examinations for subjects, particularly in a non-medical environment, such as the home or office for example. Preferably, the present invention is operable by individuals who are not medically trained, such as the subject him/herself.

BACKGROUND OF THE INVENTION

Currently, a number of different types of devices are available for monitoring human subjects in a non-invasive manner. For example, heart function can be monitored in a subject through the use of electrodes, which must be attached to the skin of the subject. Although non-invasive, such equipment is nevertheless uncomfortable for the subject, who is attached to a network of cables and wired sensors. In addition, such equipment is very expensive, limiting its use to hospitals and other medical settings in which both the cost and the discomfort of the subject can be justified. Furthermore, subjects may become anxious when examined by medical personnel, thereby significantly altering the normal readings for these subjects.

However, there are many different situations in which non-invasive monitoring of a human subject is desired. For example, such monitoring could be very useful as part of the overall health maintenance of the human subject, and could be used in order to detect any type of deterioration in the physiological condition of the subject before a concomitant deterioration in the health of the subject becomes noticeable. Examples of adverse physiological conditions which could be detected with regular non-invasive monitoring include but are not limited to excessive weight gain or less; arrhythmia and other heart conditions; incipient diabetes in the form of improper glucose metabolism; and loss of lung capacity or other problems with respiration.

Heart rate and blood pressure are important factors in determining the state of a person's health and the physical condition of a person's body in response to physical or emotional stress. Periodic monitoring of these physical parameters is particularly important for individuals having cardiac disease and/or lowered cardiac functioning, or high blood pressure. However, physically healthy individuals may also wish to periodically monitor their heart rate and blood pressure in stressful situations, for example when engaging in strenuous exercise.

In order to support regular monitoring of human subjects in their normal environment, such as in the home and at the office for example, the equipment must be non-invasive and easy to use. The equipment would then be able to monitor at least one physiological parameter of the user, without requiring the user to perform any complicated actions and/or to operate complex devices. Indeed, it would be highly preferred for the equipment to be incorporated as part of the regular daily living routine of the subject, since the requirement for any additional or special actions on the part of human subject is likely to result in decreased compliance. In addition, the equipment should be robust yet inexpensive.

For ease of use, monitoring equipments carried by the user, may be used. Those monitoring equipments are required to be ready for receiving an impromptu call initiated by the medical center. However, keeping the monitoring equipment active, ready to receive a call, reduces the live time of its battery. Therefore there is a need for a system that enables the Medical Service Center to make an impromptu call to the monitoring equipment, while the monitoring equipment is not active (in sleeping mode) without losing the information that is transferred from the Medical Center to the monitoring equipment.

Furthermore, preferably the subject should be able to transmit the collected medical information and to communicate verbally with a medical personnel. Also, medical personnel should be able to view the subject and the data being collected. In order to make the remote medical service available to wide variety of users the communication with medical personal may be carried over common communication link such as a regular telephone lines.

In case that the medical personal would like to initiate a call over common telephone line, the user has to respond to the telephone ring. In some cases the user may be in a certain physical condition that prevents him from responding to the ring. In other cases the user may be unable to control the volume of the conversation etc.

Therefore these actions should be possible remotely, without the subject being physically present with the medical personnel. Unfortunately, a system is not currently available.

Furthermore common communication system over telephone line are using DTMF signals to transfer control and/or data. On the other hand common audio/video conferencing endpoints may suppress DTMF signals. This contradiction places challenges in front of a designer who wishes to deliver affordable system for remote medical observation using audio/video/data communication over regular telephone line.

Therefore there is a need for a system and a method for audio/visual/data medical monitoring system that communicates over regular telephone line and using portable monitoring equipments. Such a system will spread the opportunity to benefit from better medical services to wide variety of population.

SUMMARY OF THE INVENTION

The present invention overcomes the deficiencies of the background art by providing a system for enabling data collection to be performed remotely while also permitting Audio/Video conferencing between the subject and the medical personnel. More specifically, the present invention is of an apparatus, which features bi-directional communication, over a regular telephone line, for transferring medical data and for communication with medical personnel. The apparatus is preferably integrated with at least one of, but more preferably both, audio and video conferencing between a remote (home and office) subject and a medical service center. The invention is particularly useful for subjects having some type of medical risk who wish to be supervised by a medical service center, as well as supervision for emergency situations.

According to an embodiment of the present invention, the system of the present invention features a remote apparatus and a medical service center apparatus, which operate to enable remote diagnostics for a subject at the home or office. The medical examinations preferably include visual and verbal communication and examinations with a two-way audio and video channel for enabling conversation between the subject and medical personnel at a medical service center. Optionally and preferably, the examinations include medical examinations using a wireless medical device located at the wrist of the subject and/or standard medical devices (such as ECG and blood pressure monitor) connected by wires or wirelessly to the home device for transferring the results to a human operated medical service center.

With an exemplary embodiment of videoconferencing between the remote subject and the medical personnel, the videoconference conversation preferably provides the medical service operator with the opportunity to perform an examination of the user. Optionally and more preferably, the examination includes a medical questionnaire regarding the medical situation of the subject, including but not limited to, the overall medical history of the subject, medications being taken, and other personal details. During a regular (voice) conversation, the medical service center's operator can then preferably examine the user visually and verbally. The operator may also optionally determine if the subject is compliant with dosing regimens for medications and/or other types of medical routines.

Optionally, the operator at the medical service center may base a decision and/or a requirement for further action according to a plurality of medical examinations, including but not limited to, reactions of the subject (verbally and visually), medical questionnaire and the measured physiological parameters with the remote medical device.

It should be noted that the terms "home", "remote" and "office" are used as examples only, in order to indicate the preferred use of the present invention outside of a profession medical environment, and are not intended to be limiting in any way.

It should be noted that the terms "subject", "user" and "patient" are used interchangeably herein. And that the terms "Medical Service Center", "Call Center" and "Medical Center" are used interchangeably herein.

Hereinafter, the terms "microprocessor", "computational device" and "computer" includes, but is not limited to, general-purpose microprocessor, a DSP, a micro-controller or a special ASIC designed for that purpose.

The method of the present invention could be described as a process for being performed by a data processor, and as such could optionally be implemented as software, hardware or firmware, or a combination thereof. For the present invention, a software application could be written in substantially any suitable programming language, which could easily be selected by one of ordinary skill in the art. The programming language chosen should be compatible with the computational device (computer hardware and operating system) according to which the software application is executed. Examples of suitable programming languages include, but are not limited to, Visual Basic, Assembler, Visual C, standard C, C++ and Java.

Other objects, features, and advantages of the present invention will become apparent upon reading the following detailed description of the embodiments with the accompanying drawings and appended claims.

BRIEF DESCRIPTION OF THE DRAWINGS

The invention is herein described, by way of example only, with reference to the accompanying drawings, wherein:

FIG. 3 is a detailed schematic block diagram of the central gateway according to an exemplary embodiment of the present invention.

DESCRIPTION OF EXEMPLARY EMBODIMENTS

Figure 1:
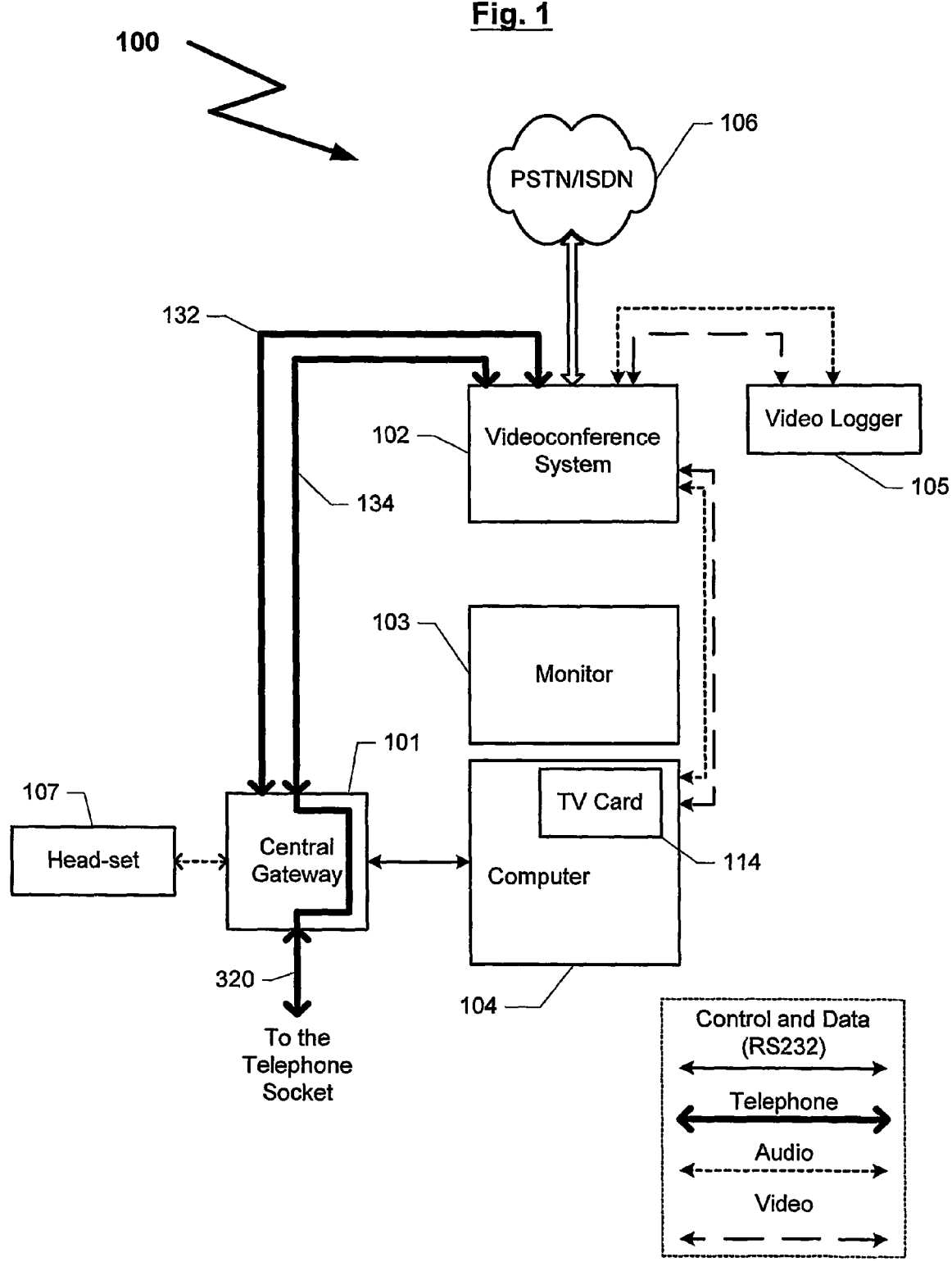
FIG. 1 is a schematic block diagram of the medical center portion an exemplary embodiment of the present invention.

Referring now to the drawing, in which like numerals refer to like parts throughout the several views, exemplary embodiments of the present invention are described.

The present invention is of a system and method for enabling data collection to be performed remotely while also permitting Audio/Video conferencing between the subject and the medical personnel. More specifically, the present invention is of an apparatus, which features bi-directional communication for transferring medical data and for Audio/Video conferencing with medical personnel. The communication may be carried over regular telephone line. The apparatus is preferably integrated with at least one of, but more preferably both, audio and video conferencing between an remote (home and office) subject and a medical service center. The invention is particularly useful for subjects having some type of medical risk who wish to be supervised by a medical service center, as well as supervision for emergency situations.

According to an embodiment of the present invention, the system of the present invention features a remote apparatus and a medical service center apparatus, which operate to enable remote diagnostics for a subject at the home or office. The medical examinations preferably include visual and verbal communication and examinations with a two-way audio and video channel for enabling conversation between the subject and medical personnel at a medical service center.

In addition, the system preferably features one or more medical devices for remote monitoring of one or more physiological parameters of the subject. Optionally and preferably, at least one device is a wireless medical device located at the wrist of the subject and/or standard medical devices (such as ECG and blood pressure monitor) connected by wires or wirelessly to the home device for transferring the results to a manual (human operated) medical service center.

Exemplary monitoring equipment may be a wristband medical device is preferably able to measure medical parameters from an array of sensors locating on the wrist. The device optionally and preferably has an activation button for starting the process of monitoring the subject, and also preferably for alerting the medical service center in case of emergency.

In one exemplary embodiment, the subject (or alternatively medical center personnel) may initiate a communication session by using a basic telephone mode of communication with the other side. The subject preferably initiates the conversation through a relatively simple operation, such as by pressing a particular key on the telephone or by pressing an activation button on the monitoring device, or alternatively through a television remote control unit, for example. The activation process preferably includes operating the user's television, adjusting it to the appropriate television channel, such as the AV channel, for example.

An exemplary embodiment of the remote portion of the present invention features a first unit with the subject (the monitoring equipment), such as a wristband device, and a second unit (the remote gateway), which is sufficiently close to the first unit, in the user's premises, but which is physically separate from the first unit. More preferably, the first unit is in communication with the second unit through a wireless connection. For this preferred embodiment, the subject preferably initiates a session by using the activation key on the wristband device (or other device according to the present invention), which may initiate a call to the remote gateway. Or alternatively, starts measuring medical parameters of the remote subject and then initiate the call. The remote gateway preferably receives the wireless transmission of the wristband and automatically starts a modem connection with the medical service center, for example by using a dial-up or TCP-IP connection.

Simultaneously or alternatively after the connection has been established, the wristband device starts collecting medical parameters from the subject. The results are then transmitted to the remote gateway. The remote gateway then preferably sends the collected physiological measurements, for example by using a modem, to a central gateway at the central gateway.

A videoconference may optionally and preferably be operated through any suitable wired communication infrastructure, such as a regular telephone line, PSTN (public switched telephone network), ISDN, Internet, LAN (local area network), cable modems and fiber-optic networks. The present invention responds to the need of a large portion of the population, especially among the elderly population that has only regular telephone line by been operating over regular telephone line. Alternatively or additionally, any type of infrastructure for wireless communications may optionally be used, such as a mobile phone, device operating according to the Bluetooth protocol, wireless LAN, and so forth.

The videoconferencing system preferably supports standard protocols, including but not limited to International Telecommunication Union ("ITU") standards H.324 (over telephone line), H.320 (over ISDN), H.323 (over IP). The ITU is the United Nations Specialized Agency in the field of telecommunications. The ITU Telecommunication Standardization Sector (ITU-T) is a permanent organ of the ITU. The ITU-T is responsible for studying technical, operating and tariff questions and issuing recommendations on them with a view to standardizing telecommunications on a worldwide basis. Additional information regarding the ITU and the standards can be found at the website address of www.itu.int.

The videoconferencing system preferably transmits and receives voice and video sub channels between the remote subject and the medical service center. The present invention may be operated using economic video conferencing system, such as but not limited to INFOVIEW manufactured by INNOMEDIA of Singapore. A common economic video conferencing system may use an external speaker and microphone in order to reduce the cost of the system. An exemplary embodiment of the present invention may use a low cost speaker and microphone using half duplex method for determining which side will be heard. The decision is based on analyzing the signal energy of both sides. The side with the higher energy is selected to be the speaker. Such a system may have limitation in communicating with a user that locates in a noisy area. For such a case a common conference system may permanently select the user as the speaker, preventing the medical operator from being heard. Therefore the present invention may have a feature that enables the medical personal, in the call center, to control the selection of the speaker. This feature is disclosed later on. The video and voice signals are then preferably transformed to a digital format using voice and video compression algorithms, enabling video and audio conversation.

Medical data may also optionally be sent over the telephone line for example by using DTMF signals or any other standard modem modulation, or alternatively or additionally by using a dedicated data link, which may optionally be additional to the voice and video signals.

According to another optional embodiment, the data may optionally be transferred through the voice link, so that when data is transferred, voice communication is blocked.

The above method of switching between audio/video signals and the data, sacrifices the real time effect of the video however it keeps the cost and the possibility to be connected over common telephone line. This feature makes the system affordable to wide range of population.

Medical data may optionally be acquired from any standard medical equipment with an analog and/or a digital, wired/wireless output. The medical data may also optionally be sent to the medical service center on-line and real time, or be stored in the remote gateway and be sent later on, off-line, while communication is established. Various types of medical devices may optionally be used in order to measure one or more medical parameters. Examples of suitable devices include but are not limited to, blood pressure meter, pulse meter, spirometer, blood glucose monitor and respiration monitor.

Examples of medical information which may be extracted from the measured physiological parameter or parameters, and sent to the medical service center, include, but are not limited to: heart rate; variability in heart rate; breathing rate; arrhythmia of the heart (if any), as well as the general rhythm and functioning of the heart; blood pressure; presence of abnormal body movements such as convulsions for example; body position; general body movements; body temperature; presence and level of sweat; SpO2 (oxygen saturation level in the blood); and glucose levels in the blood.

Most preferably, the medical equipment for monitoring the user includes a wristband device, which may measure pulse pressure and other physiological parameters as measured at the subject's wrist. This device optionally and preferably has a processing unit for acquiring the signal from an array of sensors and for extracting some medical parameters out of them and a communication module for wirelessly transmitting the calculated parameters to the remote gateway at the subject's home, more preferably by using a wireless modem, such as a radio frequency modem for example.

According to preferred embodiments of the present invention, the wrist-mounted device features one or more sensors attached to a wristband or other fastening article. The sensor(s) are preferably connected to a microprocessor, optionally by a wire but alternatively through a wireless connection. The microprocessor may optionally also be located within the wristband, or otherwise attached to the wristband. The sensor(s) preferably support automatic collection of at least one physiological measurement; more preferably, the microprocessor is able to execute one or more instructions for extracting clinically useful information about the user from such measurement(s).

The microprocessor more preferably operates a software program to process and analyze the data, which is collected, in order to compute medical information. The extracted medical information, optionally also with the raw data, is then preferably transferred to the previously described remote gateway. The remote gateway then preferably transfers the medical information and/or measured physiological parameters to the central gateway at the medical service center.

In the medical service center, the operator's station can optionally serve one or more remote subjects at any given time. As shown in FIG. 1, the operator station optionally and preferably includes a computer (104), a monitor (103), a videoconference system (102), a head set (107) and a central gateway (101). Computer (104) may have internal database or may connected to external database server (not shown), which contains data from pervious measurements of the users that are using the services of the medical center. The medical center may have extended capabilities such as video logger (105), audio logger (not shown in the drawing), load balancing (not shown in the drawing) etc.

The video and audio outputs from videoconference system (102) are connected to a video card (114) in computer (104). Video card (114) enables the operator viewing the remote subject in a display on a monitor (103), optionally together with additional medical data in other parts of the display. Other exemplary embodiments (not shown in the drawings) may use two separate monitors one for the video conferencing, as part of the videoconference system (102) and the other is used as the computer monitor for displaying the medical data.

In order to broader the use of the invention by users having only regular telephone connection, the audio/video conferencing and the medical data may be transferred over the same pair of wires (320), using H.324 protocol. The incoming telephone pair of wires (320) from the telephone socket is transferred via central gateway (101) to the main telephone plug in videoconference system (102) by telephone pair of wires (134). The sub channel telephone plug of videoconference system (102) is connected via telephone cable (132) to the Central gateway (101).

Central gateway (101) may switch between transmission of the operator's audio/video signals coming from the videoconference system (102), the audio coming from head-set (107) and the medical data coming from computer (104), more preferably according to commands from software being operated by computer (104). The switching may be done by hardware or software. For example, in cases where the communication is done over the Internet using Internet Protocol (IP), the switching may be done by soft switch. Gateway (101) is connected to computer (PC) (104) over common PC connection, like but not limited to RS232. More information about Gateway (101) is disclosed below in conjunction with FIG. 3.

Some exemplary embodiments, which are using a single monitor (103) as the monitor of the PC (104) as well as the monitor of the videoconference system 102, may use a TV card (114) for processing and displaying the Video signals coming from the Videoconference system (102). The TV card (114) may be used also for processing and producing video signal containing medical information to the videoconference system (102). The Videoconference system may transfer this information to the user or store it in the video logger (105).

Videoconference (102), in parallel to Gateway (101), may be connected over faster networks such as but not limited to ISDN (106), ATM (not shown in the drawing) etc. These networks may be used for Video/Audio conferencing with users, subjects or with other Medical Service Centers having similar capabilities.

In other exemplary embodiment PC (104) may be connected to a video camera and a microphone and by using videoconferencing software it may be used as a videoconference terminal instead of Videoconference system (102). In such a case the communication may be done over the Internet using H.323 protocol.

Figure 2:
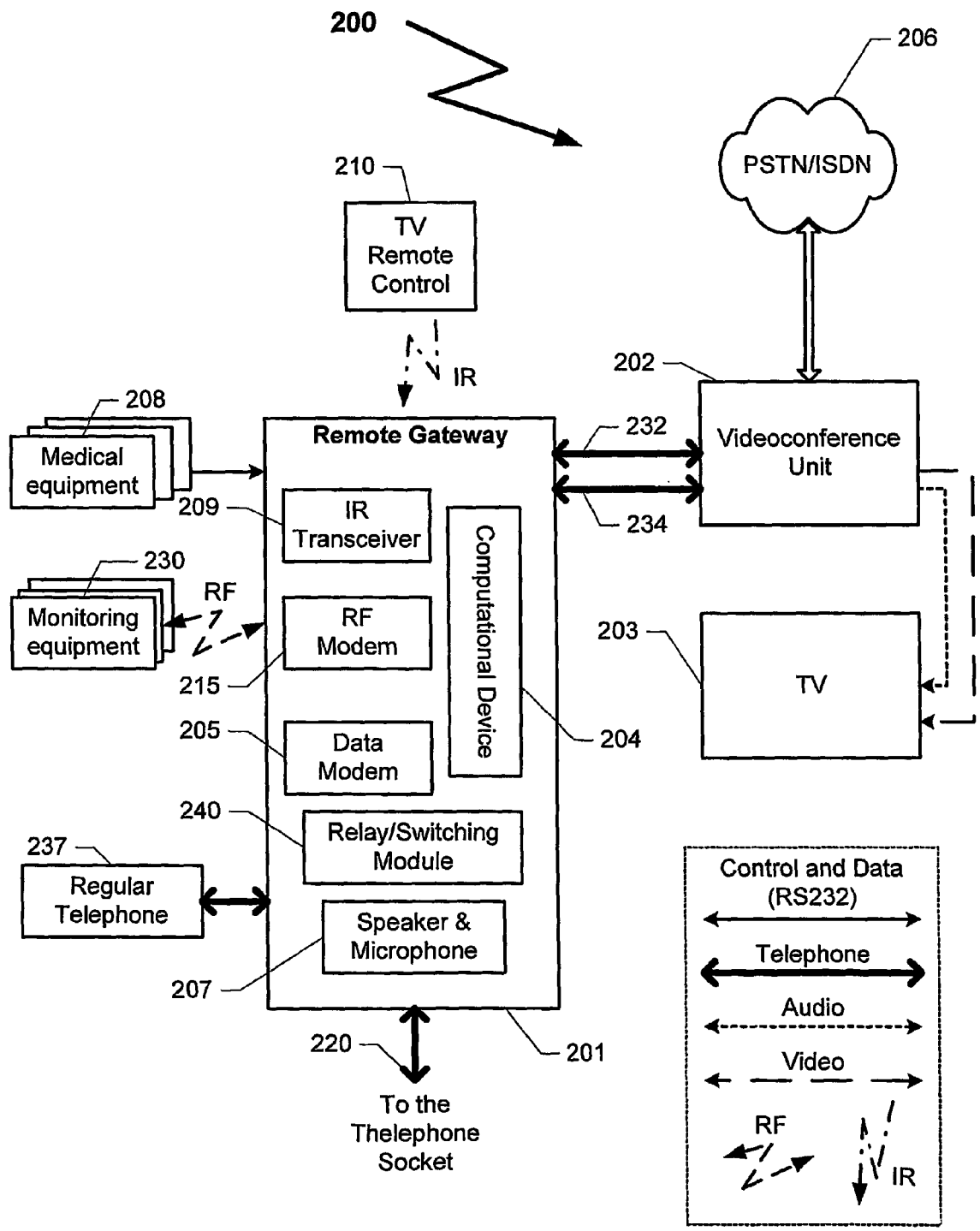
FIG. 2 is a schematic block diagram of the remote portion of a system according to an exemplary embodiment of the present invention.

An exemplary embodiment of the remote section of the present invention is illustrated in FIG. 2. The remote site at the location of the subject, such as a home or office for example, may comprise a videoconference unit (202) that is connected to a television (203), a remote gateway (201) having a speaker and a microphone (207), a regular telephone (237), at least one monitoring equipment (230) and at least one medical equipment (208).

Alternatively, the videoconference unit (202) may be connected to any one or more of a computer, PDA or a cellular telephone. The videoconference unit (202) may communicate with the medical service center (100) over faster networks such as but not limited to ISDN (206) using H.320 protocol or over IP network using H.323 protocol. However a large portion of the population, especially among the elderly population, has only regular telephone line, therefore the present invention may be operating over regular telephone line using H.324 protocol.

The telephone line (220) from the telephone socket at the remote site is connected via the remote gateway (201) and telephone cable (234) to the main telephone channel of videoconference unit (202). The telephone sub-channel plug of the videoconference unit (202) is connected by telephone cable (232) back to the remote gateway (201). Videoconference unit (202) may have an internal selector (not shown). The selector sets the connection of telephone cables (234 & 232) according to the type of communication. For vocal communication or data communication telephone cables (232 & 234) are connected to each other. For videoconferencing communication the telephone cables (232 & 234) are connected to the internal circuitry of the videoconference unit (202). Remote gateway (201), by using relay/switching module (240) routs the signal from/to telephone cable (232) either to/from data modem (205) for data communication or to/from speaker and a microphone (207) for vocal communication or to/from regular telephone (237).

Other exemplary embodiments may use a conferencing system that is based on IP protocol, such as but not limited to H.323. An IP videoconference system may include a PC, having a monitor, connected to a video camera and a microphone. The Audio/Video data is transferred over the Internet via any type of access network, such as but not limited to ISDN (206), ADSL for example, or via regular telephone pair of wires.

Remote gateway (201) is more preferably implemented as a single box containing a RF modem (215) for communication with at least one monitoring equipments (230). Remote Gateway (201) may communicate also with standard medical equipment (208) via common connection, for example RS232 or wireless connection.

Remote gateway (201) collects medical data from the at least one monitoring equipments (230), and/or from at least one standard medical equipments (208). The data is sent to computer (104, FIG. 1) at the medical service center via data modem (205), relay/switching module (240) and telephone cables (232; 234 & 220). In addition, relay/switching module (240) optionally and preferably switches between data transmission from the modem and transmission of audio coming from speaker and a microphone (207) or from regular telephone (237).

The integral speaker and a microphone (207) are used in order to facilitate vocal communication with the subject. Speaker and a microphone (207) is connected via relay/switching module (240) and telephone cable (232) to a selector (not shown) in videoconference unit (202). The selector defines whether speaker and a microphone (207) are used as independent speaker and a microphone or as the speaker and microphone of the videoconference.

Data modem (205) (such as Si2400, manufactured by Silicon Lab) is used for data communication between the remote site (200) and the medical service center (100 in FIG. 1) over regular telephone pair of wires.

Remote gateway may have an infrared transceiver (209). The infrared transceiver (209) communicates with a TV remote control unit (210) for receiving instructions from the user.

Data modem (205), wireless modem (215), relay/switching module (240) and the Infrared transceiver (209) are preferably controlled by a computational device (204), optionally and more preferably through any standard interface, such as a UART, RS232, USB interface or internal bus, for example. Computational device (204) may be general-purpose microprocessor, a DSP, a micro-controller or a special ASIC designed for that purpose etc. Computational device (204) may be located in Remote Gateway (201) as integral part of the Gateway (as shown in FIG. 2), or as external device to the remote Gateway (not shown in the drawings).

Computational device (204) may have memory, a long-term memory and/or short-term memory as RAM, SRAM, DRAM etc. and a permanent memory such as but not limited to ROM, PROM etc. The memory may be used for storing the program, setting parameters for monitoring equipment (230) and medical equipment (208). The memory may be used also for intermediate buffer for data coming from/to the Medical Center to/from the Monitoring equipments (230) and medical equipment (208). A control unit (210) for television set (203) may be used as the user interface device for activating the system functions, more preferably through infrared communication with an infrared transceiver (209), although any type of wireless communication device may optionally be substituted instead.

Computational device (204) may control a relay in the relay/switching module (240) in order to attenuate the audio to the external telephone (237) while transmitting loud DTMF tones or the modem signal to the medical service center.

FIG. 3 shows a schematic block diagram of a central gateway 101 according to an exemplary embodiment of the present invention. Central Gateway (101) is the interface between the Medical Center and the remote sites. Central gateway (101) may include: relay /switching module (303), modem (301), control tones generator (330), control panel (332), dummy load (340) and a computational device (350) that controls the operation of central gateway (101).

Central Gateway (101) is connected to the telephone network via a private switch box or directly to the telephone line. The telephone cable (320) is connected to dummy load (340) that is used to simulate "off-hook" situation in order to keep the communication during the switching between data, vocal communication or videoconferencing. The output of the dummy load (340) is connected to the main telephone channel of videoconference system (102) via telephone cable (134). The telephone sub-channel plug of the videoconference system (102) is connected by telephone cable (132) back to the central gateway (101).

Videoconference unit (102) may have a selector (not shown). The selector sets the connection of telephone cables (132 & 134) according to the type of communication. For vocal communication or data communication telephone cables (132 & 134) are connected to each other. For videoconferencing, the telephone cables (132 & 134) are connected to the internal circuitry of the videoconference system (102). Relay/switching module (303) routs the signal from/to telephone cable (132) either to/from modem (301) for data communication or to/from head-set (304) for vocal communication or from Control Tones Generator (330).

The operation of the central gateway (101) is controlled by computational device (350). Computational device (350) is connected to Computer (104 FIG. 1) using standard interface, such as RS232. Other embodiment of the present invention may use other type of connections, such as but not limited to: UART, Parallel Port and USB.

The medical operator may manually control the speaker and microphone (207 FIG. 2), at the user site, via control panel (332) that sets the Control Tone Module (330) to create the appropriate signals. The control panel (332) via computational device (350) instructs the Relay/Switching module (303) to rout the control tones to the telephone cable (320) via telephone cable (132), the selector of the videoconference system and telephone cable (134).

In other exemplary embodiments of the present invention the central gateway may be implemented by a modem module that is installed in computer (104, FIG. 1). This modem module may perform the switching operation of relay/switch module (303) and may generate various control tones. In this embodiment the keyboard of the computer may replace the control panel (332).

The initiation and performance of a communication session between the subject and the medical service center may optionally be performed according to the following example. The subject may initiate the conversation through the performance of a simple operation, for example by pressing an accepted key on the telephone, by pressing the wristband activation button, and/or alternatively through a television remote control unit. The activation process preferably includes setting of the television set of the subject to the appropriate channel. It should be noted that the medical service center may also initiate the conversation with the subject, for example in response to medical information received from a medical device (208 FIG. 2) and/or monitoring equipment (230 FIG. 2) concerning the subject, and/or in response to a lapsed period of time since the last communication session with the subject. In order to establish a call over regular telephone line both sides have to be active. One side initiates the ringing signal, for example the Central Gateway (101 in FIG. 1), and the other side, the remote gateway (201), has to respond and vice-versa. Following is an exemplary method for establishing a connection between the Medical Service Center and the Remote site. Remote Gateway (201) always sniffs the telephone line waiting for incoming call. Upon determining that ringing signal has arrived, Remote Gateway (201 FIG. 2) is waiting for few ringing cycles, for example four or eight rings allowing the user to respond. If the user responds to the ring by pulling telephone (237 FIG. 2) or any other telephone off the hook and establishes a telephone connection. Then Central Gateway (101 in FIG. 1) transmits a DTMF signal that represents unused DTMF signal, for example the signal that represent the letter 'A'. Remote Gateway (201 in FIG. 2), which permanently sniffs the telephone line, upon determining that the received signal represents the letter 'A', responds by taking control over the telephone line, at the remote site, and starts negotiating with Central gateway (101). If the user doesn't respond to the ring during the waiting period, the Remote Gateway (201) simulate the "off-hook" situation and waiting for the DTMF signal that represent the letter 'A'. Upon determining that the signal representing the letter 'A' has been received, Remote Gateway (201) starts negotiating with Central gateway (101). If the signal that represents the letter 'A' has not been received during a certain period of time, e.g. few seconds, Remote Gateway 201 returns to "on-hook" situation waiting for the next call. Other exemplary embodiments may use other tones than the tones that represent the 'A'.

In an exemplary embodiment of the present invention, the remote site may automatically initiate a call to the Medical Service Center in certain occasions, for example: upon determining that the memory of the remote gateway (201) is full with new measurements, or upon determining that at least one of the medical measurement are above or below certain conditions.

Preferably, the subject has at least one monitoring equipments (230 FIG. 2), which is in physical contact with the subject for measuring one or more physiological parameters. The monitoring equipment preferably communicates with the computational device (204 in FIG. 2) of the apparatus, preferably through the wireless modem (215 FIG. 2), for example. The computational device (204) upon determining that the measurement are out of the normal range, may instruct the remote gateway (201) to call the medical service center, and optionally and more preferably activates the speaker and microphone. The data modem is then activated, or "goes off-hook", and preferably places a voice call without waiting for acknowledgement. If the communication line, such as the PSTN telephone line for example, is busy, data modem preferably redials. Optionally and more preferably, the data modem stops attempting to place the call after a number of failed attempts, such as three attempts for example.

According to another option, the detection of a DTMF is optionally and preferably used as the call connection acknowledgement. If the remote gateway senses that another telephone went "off-hook", it optionally continues to monitor the line for DTME commands. Throughout the call, the remote gateway disconnects the call and returns to on-hook in one of two events: not detecting DTMF for pre-defined time or detecting a busy tone.

Once the telephone call has been successfully placed by the remote gateway, the telephone at the medical service center is activated. The central gateway preferably transmits the identification of the user (user's ID) to the central computer PC (104 FIG. 1). This computer then preferably displays the subjects records to the medical service center operator.

The operator then optionally and preferably instructs the subject to sit still and to perform the medical measurement with the medical equipment and/or the monitoring equipments. The operator may initiate transferring the medical data from the remote gateway through a command to the central computer. PC (104) may instruct the central gateway (101 FIG. 1) to send a DTMF trigger sequence to the remote side and to attenuate the operator telephone signals.

The remote gateway then may switch to data mode, for example by attenuating the telephone signals of the subject, and by disabling the speaker and microphone. The remote gateway then preferably sends the measured data to the medical service center and switches back to voice mode. The modem goes off-hook for the duration of the data transfer.

Then, the operator may switch to video mode. Switching to video mode is preferably performed through a command to the central computer (104), which instructs the central gateway to send DTMF commands to switch to video mode. The low-speed modem goes off-hook, dials the DTMF code and returns to on-hook.

As an option, the central computer can preferably switch the videoconference unit to external video source mode, such as video logger (105 FIG. 1) in order to optionally send video data to the subject during the transfer of the medical data The call is optionally and more preferably terminated from the medical service center. The remote gateway preferably detects a disconnect DTMF command code or the busy tone and switches to on-hook mode.

At any time, the subject and/or the medical doctor of the subject may examine the medical file of the subject, for example by retrieving this information from a Web based medical server (not shown in the drawings) by connecting to the network, such as the Internet for example. The Web based medical server is a logical part of the medical center. In medical center having a computer (104) with internal database, the web server is connected to computer (104 FIG. 1). In cases where external database server (not shown) are used, the Web server is connected to the external database server. The other side the web server is connected, via an Internet service provider, to the Internet. The data, in the web server, is more preferably protected by a password. The server is more preferably Web-protocol based, such as HTTP based for example. The server can optionally and more preferably be accessed by a regular Web browser (such as a standard Internet Explorer by Microsoft for example). The Web server may optionally provide the information as a Web site. At the Web site, the subject and/or doctor (or other medical personnel) may optionally retrieve a full report on the current status and previous measurements of the subject, and/or to chart a graph and/or to add comments, for example.

Common speaker and microphone is using half duplex method to overcome the echo that may be generating in a speaker and microphone. This method monitors the signal energy in both sides and allows the stronger side to be the speaker. However, the operator at the call-center has a manual possibility to override the automatic decision and be the speaker by using a Push To Talk button, for example. In remote medical communication the user may be in a certain physical condition that is unable to control the speaker and microphone. Therefore the present invention allows the operator, in the Medical Service Center, to control the remote speaker and microphone. The Operator may command computer (104 FIG. 1) to instruct the Computational Device (204 FIG. 2) in the remote site to set the remote speaker and microphone (207) accordingly. The command may pass via modem (301 FIG. 3) to modem (205) at the remote Gateway (201) and from there to the computational device (204).

In cases that the Audio/video signals are carried over a pair of telephone wires using H.324 protocol, using common DTMF signals may be problematic, since common encoders of the videoconference system suppress DTMF signals. The present invention overcomes this limitation by using proprietary control tones that differ from DTMF tones. For example frequencies like 2.4 KHz, 3.0 KHz etc. The operator may use a 'Remote Site Push to Talk Button'. Pressing this button activates an electronic circuit that generates the proprietary control tones; those tones are transferred as audio signals via the videoconference devices (102 FIG. 1 & 202 FIG. 2) to Remote Gateway (201) that analyzes the control tones and control the speaker and microphone (207) accordingly.

To save battery the monitoring equipment usually is in "sleeping mode", during this mode only an internal timer, for date and time, (software or hardware) is active and the monitoring equipment (230) is disconnected from the external world. The sleeping period is terminated upon receiving a trigger from the internal timer or by manual activation, such as pressing the panic push button at the monitoring equipment. Upon activated the monitoring equipment (230) starts a measuring cycle and initiates a communication link with the Remote Gateway (201) via RF Modem (215).

Among its other tasks, Remote Gateway (201) is used as an intermediate buffer that stores command and data coming from the Medical Service center to the monitoring equipment until receiving a request from the monitoring equipment to set communication with the remote gateway. The information coming from the Medical Center may include data like but not limited to type of measurements that are needed, setting the sleeping period, setting the internal clock of the monitoring equipment etc. Upon setting the communication between the two, the monitoring equipment (230) asks the Remote gateway (201) to retrieve the information that have been received from the medical center during the recent sleeping period. In this method of operation, the Remote Gateway (201) is used as an intermediate buffer for data coming from both sides either from the monitoring equipment or from the medical center. The remote gateway eliminates the need for the medical center as well as the monitoring equipment (230) to be on-line on the same time.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

What is claimed is:

1. A patient medical monitoring and reporting system comprising:
    a patient medical monitoring and processing unit which, when located on a subject, measures a physiological parameter of a subject to form physiological data;
    a remote communication gateway at the patient premises, wherein said remote communication gateway receives said physiological data from said patient medical monitoring and processing unit;
    a central bidirectional streaming and physiological data medical service gateway connected with said remote communication gateway via a public communication network, said central medical gateway and said remote communication gateway communicating said physiological data and communicating bi-directional streaming conferencing information, said streaming conferencing information comprising at least one of audio information and video information; and
        a microcontroller configured to switch said system between communicating said physiological data and communicating said bi-directional streaming conferencing information.

2. The system of claim 1, wherein said central gateway includes a Control Tone Generator, and said remote gateway includes a Computational Device useful for tone decoding, said tone decoding being usable in said remote controlling of said alternating.

3. The system of claim 1, wherein said remote gateway and said central medical service gateway include video conference means useful for video and audio conference sessions.

4. The system of claim 1, wherein said central gateway includes a Dummy Load module useful for keeping a phone call off-hook.

5. The system of claim 1, wherein said central gateway and said remote gateway include relay/switching modules useful for switching between at least two of: audio, data and video conference.

6. The system of claim 1, wherein said remote gateway includes a speaker and a microphone useful for speaker phone capabilities.

7. The system of claim 1, wherein said central medical service gateway includes a PC and a TV card within said PC.

8. The system of claim 1, further comprising:
    a timer installed in said at least one patient medical monitoring and processing unit for activating said monitoring unit on scheduled times as requested by said central medical service gateway.

9. A system according to claim 1, wherein said central medical service gateway is configured to receive a call bearing data, over said public communication network, which is initiated by said patient medical monitoring and processing unit, and to store said data in association with said central medical service gateway until transferred later on to said at least one patient medical monitoring and processing unit, upon said unit's request, and
    wherein said remote gateway is configured to receive a call bearing data, over said public communication network, which is initiated by said at least one patient medical monitoring and processing unit, and to store said data in association with said remote gateway until transferred later on to said central medical service gateway upon request.

10. A system according to claim 1, further comprising:
    a Dummy Load module within said central gateway;
    video conference means within said remote gateway and said central medical servicegateway for communication using a video mode; and
    Relay switching modules within said central gateway and said remote gateway;
    wherein said dummy load module is usable via said relay switching modules to supply a dummy load to hold a telephone call while carrying out said alternating.

11. A system according to claim 1, further comprising:
    a connection via said public communication network between said remote gateway and said central gateway;
    a speaker and a microphone within said remote gateway; and
    a Control Tone Generator within said central gateway and Computational Device useful for tone decoding within said remote gateway configured such that the operation of said speaker and microphone is controllable using said Control Tone Generator and said Computational Device.

12. A system according to claim 11 wherein said operation is configured to establish the direction of a voice call.

13. A system according to claim 1,wherein:
    i) said monitoring unit is configured to retain a sleeping mode until it is triggered by said patient;
    ii) said monitoring unit is configured to perform medical measurements and to store them on said monitoring unit;
    iii) said monitoring unit is configured to send measurements to said remote gateway, and said remote gateway is configured to buffer said measurements within said buffer unit;

iv) said monitoring unit is configured to request said remote gateway to retrieve commands stored on said buffer unit;

v) said remote gateway is configured to send said measurements upon a request of said central medical service gateway;

vi) said central medical service gateway is configured to store said measurements, and vii) said central medical service gateway is configured to send commands to said monitoring unit via said remote gateway using said buffer unit.

14. A system according to claim 1, further comprising:
a connection via a telephone network; and
a speaker and a microphone within said remote gateway;
wherein said remote gateway is configured to automatically answer a call from said central medical service gateway and to activate said microphone and speaker.

15. A system according to claim 1, further comprising:
a connection via a telephone network;
conference means within said remote gateway and said central medical service gateway; and
said medical service gateway including a PC and a TV card within said PC;
wherein said PC is configured to generate audio and video signals and to send said audio and video signals through said TV card to said medical service gateway videoconferencing equipment and there from to videoconferencing equipment at said remote gateway.

16. A patient medical monitoring and reporting system according to claim 1, wherein said remote gateway is operative to perform at least one of:
automatically initiating a call to said central gateway and executing at least one of:
transferring said received measurement; and
transferring said stored data; and
automatically answering a call from said central gateway and executing at least one of:
transferring said received measurement; and
transferring said stored data.

17. A system according to claim 1 wherein said remote gateway and said central gateway are operative to communicate said measured physiological parameter, and to provide video-conferencing, alternating over the same communication session.

18. A system according to claim 17, wherein said central gateway is configured to control said remote gateway to synchronously alternate between said communicating said measure physiological parameter and said video-conferencing.

19. A system according to claim 18, wherein said central gateway includes a switch and a dummy load useful for keeping a telephone call off-hook.

20. A patient medical monitoring and reporting system according to claim 1 wherein said controllably alternating communication comprises at least one of:
remotely controlling said alternating of said communication; and
manually controlling said alternating of said communication.

21. A patient medical monitoring and reporting method comprising:
measuring a physiological parameter of a subject, said measuring being made using a patient medical monitoring and processing unit located locally at said subject, to form physiological data;
remotely receiving said physiological data from said subject at a remote gateway at premises of said subject; and
using a central bidirectional streaming and physiological data medical service gateway which is connected with said remote communication gateway via a public communication network, said central medical gateway and said remote communication gateway communicating said physiological data and further communicating bi-directional streaming conferencing information, said streaming conferencing information comprising at least one of audio information and video information;
the method further comprising using a controller to controllably alternate between communicating said physiological data and communicating said bi-directional streaming conferencing information.

22. The method of claim 21, wherein said central gateway includes a Control Tone Generator, and said remote gateway includes a Computational Device useful for tone decoding, said tone decoding being usable in said remote controlling of said alternating.

23. The method of claim 21, wherein said remote gateway and said central medical service gateway include video conference means useful for video and audio conference sessions.

24. The method of claim 21, comprising providing, at said remote gateway, a speaker and a microphone for speaker phone capabilities.

25. The method of claim 21, comprising receiving, at said central medical service gateway, a call bearing data, over said public communication network, which is initiated by said patient medical monitoring and processing unit, and storing said data in association with said central medical service gateway until transferred later on to said at least one patient medical monitoring and processing unit, upon said unit's request, and
wherein said remote gateway receives a call bearing data, over said public communication network, which is initiated by said at least one patient medical monitoring and processing unit, and stores said data in association with said remote gateway until transferred later on to said central medical service gateway upon request.

26. The method of claim 21, further comprising providing:
a connection via a telephone network; and
a speaker and a microphone within said remote gateway;
and at said remote gateway automatically answering a call from said central medical service gateway and activating said microphone and speaker.

27. The method of claim 21, comprising carrying out, at said remote gateway, at least one of:
automatically initiating a call to said central gateway and executing at least one of:
transferring said received measurement; and
transferring said stored data; and
automatically answering a call from said central gateway and executing at least one of:
transferring said received measurement; and
transferring said stored data.

28. The method of claim 21, wherein said controllably alternating communication comprises at least one of:
remotely controlling said alternating of said communication; and
manually controlling said alternating of said communication.

29. The system of claim 1, wherein said microcontroller comprises a switch for controllably switching said system between communicating said physiological data and communicating said bi-directional streaming conferencing information.

30. The system of claim 1, wherein said remote communication gateway is operative to control said switching of said central gateway between communicating said physiological data and communicating said bi-directional streaming conferencing information.

31. The system of claim 30, wherein said remote communication gateway is operative to switch between communicating said physiological data and communicating said bi-directional streaming conferencing information under user control.

32. The system of claim 1, wherein said central gateway is configured to control said switching of said remote communication gateway between communicating said physiological data and communicating said bi-directional streaming conferencing information.

33. The system of claim 32, wherein said central gateway is operative to switch between communicating said physiological data and communicating said bi-directional streaming conferencing information under user control.

34. The system of claim 1, wherein said microcontroller is configured to switch between communicating said physiological data and communicating said bi-directional streaming conferencing information over a single call.

* * * * *